US007026623B2

(12) United States Patent
Oaknin et al.

(10) Patent No.: US 7,026,623 B2
(45) Date of Patent: Apr. 11, 2006

(54) EFFICIENT SINGLE PHOTON EMISSION IMAGING

(76) Inventors: Jacob Oaknin, Geva Carmel, P.O. Box 41, Hof HaCarmel, 30855 (IL); Shoulamit C. Shwartz, Hasela St. P.O. Box 183, Atlit, 30300 (IL); Israel Ohana, 5 Peretz Bernstein Street, Haifa (IL) 34981

( * ) Notice: Subject to any disclaimer, the term of this patent is extended or adjusted under 35 U.S.C. 154(b) by 0 days.

(21) Appl. No.: 10/752,978

(22) Filed: Jan. 7, 2004

(65) Prior Publication Data

US 2005/0145797 A1    Jul. 7, 2005

(51) Int. Cl.
G01T 1/166    (2006.01)

(52) U.S. Cl. ................................. 250/363.04

(58) Field of Classification Search ........... 250/363.03, 250/363.04, 363.02, 370.13, 363.09

See application file for complete search history.

(56) References Cited

U.S. PATENT DOCUMENTS

| H12 H | * | 1/1986 | Bennett et al. ......... 250/363.09 |
| 5,448,073 A | * | 9/1995 | Jeanguillaume ........ 250/363.02 |
| 5,587,585 A | | 12/1996 | Eisen et al. |
| 5,596,198 A | * | 1/1997 | Perez-Mendez ........ 250/370.11 |
| 5,841,140 A | | 11/1998 | McCorskey et al. |
| 6,028,313 A | | 2/2000 | McDaniel |
| 6,040,580 A | | 3/2000 | Watson et al. |
| 6,242,743 B1 | | 6/2001 | De Vito et al. |
| 2003/0136912 A1 | * | 7/2003 | Juni ...................... 250/363.04 |
| 2004/0208276 A1 | * | 10/2004 | Kaufman ...................... 378/4 |

OTHER PUBLICATIONS

U.S. Appl. No. 10/333,947, filed Jan. 2003, Shwartz et al.
"ACC/AHA/ASNC Guidelines for the clinical use of Cardiac Radionuclide Imaging" American College of Cardiology Foundation and the American Heart Association, Inc. 2003. p. 42, and the publication as a whole.
ACR Practice Guideline for the Performance of Tumor Scintigraphy (with Gamma Cameras), American College of Radiology, revised 2000, effective Jan. 1, 2001, p. 555 and the publication as a whole.
Society of Nuclear Medicine Procedure Guideline for General Imaging, version 3.0, approved May 30, 2004. On p. 5, under the heading "B. SPECT Imaging", paragraph numbered 1.d. and the pulication as a whole.

(Continued)

Primary Examiner—David Porta
Assistant Examiner—Marcus Taningco
(74) Attorney, Agent, or Firm—Shalom Wertsberger; Saltamar Innovations

(57) ABSTRACT

A method of diagnostic imaging in a shortened acquisition time for obtaining a reconstructed diagnostic image of a portion of a body of a human patient who was administered with dosage of radiopharmaceutical substance radiating gamma rays, using SPECT. The method comprises acquiring photons emitted from said portion of the body, by means of a detector capable of converting the photons into electric signals, wherein the total time of photon acquiring is substantially shorter than the clinically acceptable acquisition time; processing said electric signals by a position logic circuitry and thereby deriving data indicative of positions on said photon detector crystal, where the photons have impinged the detector; and reconstructing an image of a spatial distribution of the pharmaceutical substance within the portion of the body by iteratively processing said data.

28 Claims, 7 Drawing Sheets

OTHER PUBLICATIONS

"Physics in Nuclear Medicine, Second Edition", James A. Sorenson and Michael E. Phelps, W.B. Saunders Company, Philadelphia, PA, 1987, ISBN 0-8089-1804-4, pp. 307-309 and 424-425.

C.E. Metz, F.B. Atkins and R.N. Beck, "The Geometric transfer function component for scintillation camera collimators with straight parallel holes," Phys. Med. Biol., 1980, v. 25, p. 1059-1070.

D.L. Bailey, B.F. Hutton & P.J. Walker, "Improved SPECT Using Simultaneous Emission and Transmission Tomography", Journal of Nuclear Medicine, 1987, 28: 844-851.

L. A. Shepp and Y. Vardi, "Maximum likelihood reconstruction for emission tomography," IEEE Transactions on Medical Imaging, 1982, v. 1, p. 113-122.

K. Lange and R. Carson, "EM reconstruction algorithms for emission and transmission tomography," Journal of Computer Assisted Tomography, 1984, v. 8, p. 306-316.

P.J. Green, Bayesian reconstructions from emission tomography data using a modified EM algorithm, IEEE Transactions on Medical Imaging, Mar. 1990, v. 9, p. 84-93.

P.J. Green, On the use of the EM algorithm for penalized likelihood estimation, J. Roy. Statistical Society (B), 1990, 52, No. 3, pp. 443-452.

D. German and G. Reynolds, Constrained Restoration and the Recovery of Discontinuities, IEEE transactions on Pattern Analysis and Machine Intelligence, Mar. 1992, v. 14, p. 367-383.

* cited by examiner

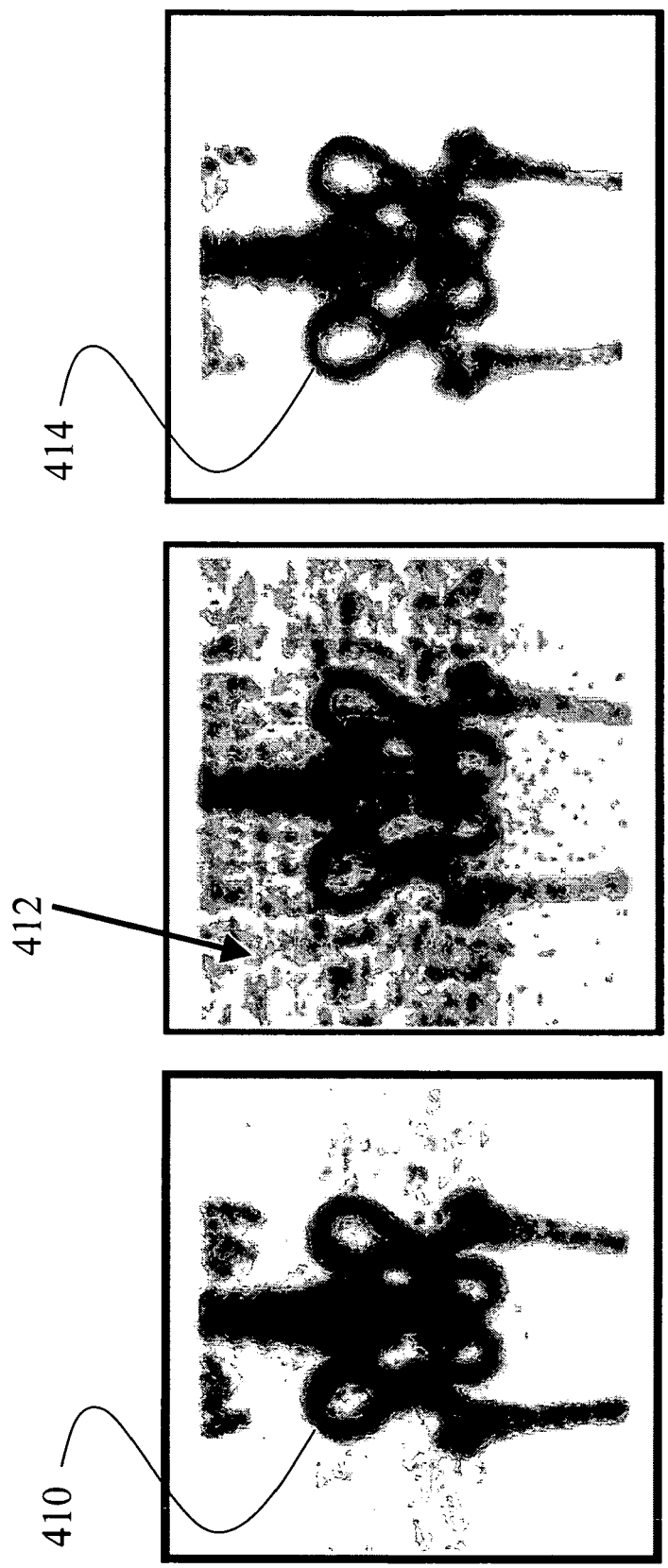

EFFICIENT SINGLE PHOTON EMISSION IMAGING

FIELD OF THE INVENTION

The present invention relates to nuclear medicine imaging More particularly it relates to an efficient method for single photon emission computerized tomography imaging.

BACKGROUND OF THE INVENTION

Nuclear Medicine imaging techniques enable to acquire functional information on a patient's specific organ or body system. This functional information is attained from analysis of internal radiation from pharmaceutical substance administered to the patient, which is labelled with a radioactive isotope. The radioactive isotope decays, resulting in the emission of gamma rays, thus providing information on the concentration of the radiopharmaceutical substance in regions of the patient's body. An instrument for the detection of gamma ray emissions of the radiopharmaceutical substance administered in the body is known as gamma camera. The Gamma camera collects gamma ray photons that are emitted from the patient's body, and the collected data is used to reconstruct an image or a series of images of the place in the body from which the gamma rays are originated. From this picture a physician can determine how a particular organ or system is functioning.

The main components making up a conventional gamma camera are photon detector crystal or detector array, a collimator for limiting the detection of incident gamma rays to a predetermined view angle, position logic circuits and data analysis computer. Depending on the type of the detector crystal, conventional gamma camera may or may not include a photo-multiplier tube array.

A gamma ray photon that has passed through the collimator interacts with the detector crystal by means of the Photoelectric Effect or Compton Scattering with ions of the crystal. These interactions cause the release of electrons, which in turn interact with the crystal lattice to produce light, in a process known as scintillation. Since only a very small amount of light is given off from the crystal, photo-multiplier tubes are normally attached to the back of the crystal. Typically, a conventional gamma camera has several photo-multiplier tubes arranged in a geometrical array. The position logic circuits that follow the photo-multiplier tube array receive electrical impulses from the tubes and determine where each scintillation event occurred in the detector crystal. Finally, in order to deal with the incoming projection data and to process it into a meaningful image of the spatial distribution of activity within the patient, a processing computer is used. The computer may employ various processing methods to reconstruct an image.

Different collimators are used in gamma cameras to limit the detection of photons to incidence range of predetermined angles. A parallel-hole collimator is typically made of lead or tungsten and has thousands of straight parallel holes in it, allowing only those gamma rays travelling in certain directions to reach the detector. As a result, the ratio of emitted versus detected photons may reach as high as 10000 to 1. In order to decrease this ratio, converging or diverging hole collimators, for example, fan-beam and cone-beam are also known in the art. The usage of these collimators increases the number of photon counts, which consequently improves sensitivity. Sensitivity, however, is inversely related to geometric resolution, which means that improving collimator resolution (i.e., having smaller diameter holes) decreases collimator sensitivity, and vice versa.

Single photon emission (SPE) imaging is a known nuclear medicine imaging technique. Several modes of SPE imaging are in use:

One of them is Single Photon Emission Computerized Tomography (SPECT). In this technique the gamma camera is rotated around the region of interest in the patient's body, and data is collected at several angular positions (hereafter referred to as angular projections). A fully three dimensional image is reconstructed from these angular positions.

SPECT is considered to be a very useful technique and a good tool for obtaining functional diagnostic information, however it requires the collection of large number of emitted photons (large statistics) and this means that in order to obtain the required number of photons, a long acquisition time is necessary. Long acquisition time means that the patient is subjected to a relatively long period of discomfort, and, furthermore, the overall number of patients who can be imaged in a given time is relatively small—a feature that many medical institutes and hospitals regard as an extremely unfavourable and undesirable situation.

Multi-detector cameras are capable of acquiring more photons per second than single detector cameras. Most popular are dual-detector cameras in which the two detectors are mounted in two different positions around the patient and are rotated simultaneously around him. The effective acquisition time of a dual-detector camera is that of a single-detector camera. For example, acquisition time of 10 minutes by a dual detector camera will result in effective acquisition time of 20 minutes.

Filtered Back Projection (FBP) is the most popular method of reconstruction of three-dimensional image from the acquired data set of angular projections. This method requires relatively short calculation time and is readily available commercially. FBP algorithms suffer from image quality degradation when the number of angular projections is low or when the angular distribution is irregular.

Nuclear emission is a stochastic process, thus the relative statistical noise associated with each acquired angular projection increases as the number of acquired photons used to form the projection decreases. Applying FBP algorithm on data set that includes high statistical noise causes degradation to the quality of the reconstructed image.

The current use of collimators results in a rather low detection efficiency of conventional SPECT, which leads to a prolonged data acquisition time and the need to administer high dosage of the radiopharmaceutical substance. The dosage used is determined by maximal radiation that can be safely tolerated by a patient.

Generally, each detector of a gamma camera is capable of being equipped with one of several interchangeable collimators, which are changed in order to match the type of diagnostic procedure. The collimators used in standard size gamma camera are heavy and costly.

The combination of dosage, collimator type and acquisition time, which sets image quality, that is adequate for specific diagnostic procedure was determined by nuclear imaging professionals during years of experience.

Another parameter that strongly affects both data acquisition time and image quality is the number of pixels in the image.

In pixilated detectors, such as solid-state detectors, the number of pixels in the reconstructed image is limited by the number of pixels of the detector. In scintillation-based detectors, the acquired data undergoes discretization process in which the photons are binned according to their position on the detectors. Similarly, the reconstruction of a three dimensional image is also set to a finite matrix of voxels. Since the reconstruction process often includes Fourier Transformation, the matrix size is generally chosen to be in the form of $2^m$ where m is an integer. Practical matrix sizes that are typically used are 64×64 and 128×128.

The discretization process may be done during the data acquisition. Alternatively, the location on the detector of each impinging photon may be saved at full spatial resolution in a file as a list of events, optionally with additional information such as its energy or the position of the detector or the time of the event. Later, the list of events is analyzed and the discretization process is performed off line. This method of data collection and processing is known as List-Mode acquisition.

Due to the discretization process, the average number of acquired photons per pixel is inversely proportional to the number of pixels in the matrix:

$$Av=Num/(2^m)^2$$

Where Num is the number of photons acquired and Av is the average number of photon in a pixel.

Since radioactive emission is a stochastic process, the relative stochastic noise associated with the number of photons counted in each pixel decreases as the number of counted photon increases. Image quality is strongly adversely affected by that noise. Thus, in situations where the number of acquired photons is small, such as in short duration acquisition, a smaller matrix size is chosen.

However, the resolution of the image is limited by the size of the pixels, so that larger matrices are desirable in situations where small features in the image have to be resolved.

Iterative reconstruction methods are used for SPECT. PCT/IL01/00730, published as WO 02/12918, presently allowed U.S. application Ser. No. 10/333,947, filed Jan. 22, 2003, and incorporated herein by reference, discloses methods for image reconstruction that result in enhanced three-dimensional nuclear image. These methods make uses and take advantage of collimators whose sensitivity is higher than collimators traditionally used in hospitals in order to collect larger number of detected photons within the data set, used for reconstruction of the enhanced three-dimensional image of superior quality.

In cardiac SPECT imaging the radiopharmaceutical distribution in the myocardium of a patient is imaged. Since the heart is beating, the heart wall motion blurs the image that is reconstructed from the accumulated data. In Gated SPECT imaging, the imaging is synchronized with the heart movement-cycle using electrocardiogram (ECG) signal.

In gated SPECT, each angular projection is divided to S sub-projections. All the sub-projections belonging to the same projection are acquired at the same angle, but at different times. Using the patient's ECG signal, the heartbeats are detected and the time between the end diastolic and end systolic phases is divided by S segments (typically S=8). Data acquired in each time segment is accumulated in the corresponding sub-projection.

Image reconstruction is done separately for the S groups of sub-projections, each showing different and relatively un-blurred phase of the heart motion. In addition, it is customary to reconstruct an image of the totality of all the acquired data. This image, although blurred by the motion, has less statistical noise. U.S. Pat. No. 6,507,752, incorporated herein by reference, for example, demonstrates a method of quantitative determination of cardiac muscle control by electrocardiogram synchronized traverse tomogram.

Tissue of various organs in the patient body attenuate gamma photons. This attenuation causes degradation of image quality due to loss of photons and more importantly, image distortion due to varying amount of attenuation between different organs of the body and the detector as it views the body from various direction.

Attenuation correction methods may be used to correct the distortion caused by tissue gamma absorption. However, in order to address the attenuation problem, an attenuation map—a quantities description of the attenuation within the patient's body is needed. One method for obtaining patient attenuation map is to position the patient between a radioactive source and the detector so that gamma photons pass through the patient body and get detected by the detector. The patient body is then scanned and angular attenuation projections are calculated from comparing the number of photons transmitted through the patient to the number of photons detected in the absence of the patient. Since attenuation through the dense parts of the body is considerably high the number of transmitted photons is low and thus image quality of the reconstructed attenuation map is limited by the time spent on acquiring the transmission data.

When emission data is gated, attenuation data may have to be gated as well to reflect the motion of the patient chest during heartbeats. For example, U.S. Pat. No. 6,429,434, incorporated herein by reference teaches a technique to address the attenuation problem.

SUMMARY OF THE INVENTION

In several clinical settings, the critical parameter in SPECT imaging is the data acquisition time. Shorter acquisition time is important for at least the following reasons:

Patient discomfort—During SPECT data acquisition the patient must stay motionless usually laying on an uncomfortable examination table.

Image quality—During long acquisitions, some patients do move causing image blurring.

Patient safety—Some patients, such as children, must be sedated or restrained to prevent movements.

Camera throughput—Image reconstruction, image processing and interpretation of clinical findings is usually done off-line in a remote data-processing station, while the camera is capable of acquiring new data.

Image quality attained by conventional imaging routine matches the necessary for successful diagnostics, and although any improvement of image quality is welcome, it is generally not mandatory.

There is thus provided, in accordance with some embodiments of the present invention, a method of shortening the data acquisition time while at least maintaining and possibly enhancing image quality of a SPECT nuclear emission image acquired by a gamma camera.

In some embodiment of the current invention, a method of shortening data acquisition time for obtaining a reconstructed image of a portion of a body of a patient who was administered with clinically acceptable dosage of radiopharmaceutical substance radiating gamma rays, using SPECT (single photon emission computerized tomography), for determination of functional information thereon, comprising the steps of: acquiring photons emitted from said portion of the body, by means of a detector capable of converting the photons into electric signals, wherein the total time of photon acquiring is equal or less than two thirds of the clinically acceptable acquisition time; processing said electric signals by a position logic circuitry and thereby deriving therefrom data indicative of positions on said photon detector crystal, where the photons have impinged the detector; and reconstructing an image of a spatial distribution of the pharmaceutical substance within the portion of the body by iteratively processing said data.

In some embodiments of the current invention, the iteratively processing said data is done in conjunction with weight values, derived from functions of either solid angles or solid angles and distances between different discrete elements of the portion of the body and corresponding discrete elements of the projection of the portion of the body on the detector.

In some embodiments of the current invention the total effective time of photon acquiring is equal or less than two thirds of the clinically acceptable acquisition time used in the art. In other embodiments of the current invention, the effective time of photon acquiring is equal or less than one half or even equal or less than one third of the clinically acceptable acquisition time without adversely affecting the image quality.

In some embodiments, acquiring photons emitted the examined portion of the body comprises of acquiring adjacent angular projection separated by at least 5 degrees.

In other embodiments, acquiring photons emitted from said portion of the body comprises of acquiring adjacent angular projection separated by at least 6 degrees, 8 degrees or even separated by at least 9 degrees.

In some embodiments of the current invention, time of photon acquiring is such that the total effective acquisition time is equal or less than less than 10 minutes. In other embodiments, the total time of photon acquiring is such that the total effective acquisition time is equal or less than 8 minutes, 7 minutes or even less or equal to 6 minutes.

In another embodiments of the current invention, data acquisition is performed in List-Mode fashion, and processing said data comprises arranging the data in angular projections.

In yet another embodiments of the current invention a detector is continuously rotates about the patient while data is being acquired.

More objects and advantages of the present invention will become apparent from the following detailed descriptions when read in conjunction with the accompanying drawings.

BRIEF DESCRIPTION OF THE DRAWINGS

In order to better understand the present invention, and appreciate its practical applications, the following Figures are provided and referenced hereafter. It should be noted that the Figures are given as examples only and in no way limit the scope of the invention. Like components are denoted by like reference numerals.

FIG. 4a is a reconstructed clinical image of a pelvis of child taken with full set of 120 angular projections and reconstructed using Filtered Back Projection (FBP) algorithm as known in the art.

FIG. 4b is a reconstructed image of the same pelvis of FIG. 4a taken with reduced set of 40 angular projections and reconstructed using FBP algorithm; showing characteristic artifacts and reduced image quality.

FIG. 4c is a reconstructed image of the same pelvis of FIG. 4a taken with the reduced set of 40 angular projections as in FIG. 4b and reconstructed using iterative algorithm according to the current invention, not showing the artifacts and with superior image quality.

DETAILED DESCRIPTION OF THE INVENTION AND PREFERRED EMBODIMENTS

The general objective of the present invention, which will be described subsequently in greater detail, is to provide a novel technique for acquisition and reconstruction of SPECT single photon emission images in which the duration of the time consuming data acquisition step is substantially reduced (with respect to known techniques), thus decreasing patient discomfort, potentially improving image quality and increasing the Gamma camera's throughput.

Figure 1A:
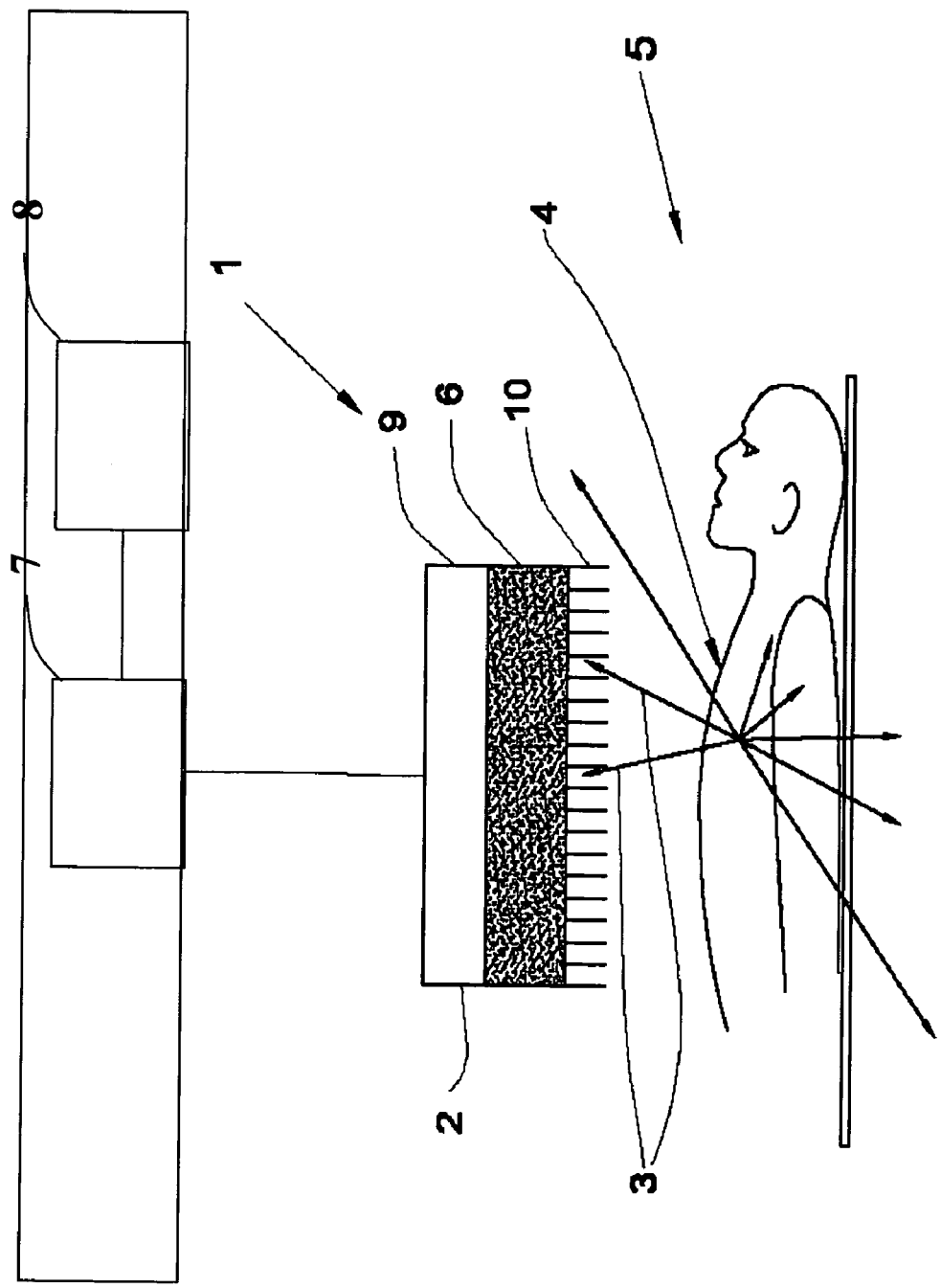
FIG. 1a is a pictorial illustration of the operation of a gamma camera.

Reference is first made to FIG. 1a depicting a side view of a simplified schematic diagram of gamma camera in accordance with the present invention, for obtaining a SPECT image of a portion of a body that has been administered by a radiopharmaceutical substance radiating gamma rays.

The gamma camera 1 comprises a detector 2 mounted above an inspected portion 4 of a body 5, position logic circuitry 7 and a data analysis computer 8, all connected appropriately.

Detector 2 includes at least one photon detector crystal 6 facing the portion 4 of body 5. For example, detector 2 may be of the kind used in a known per se Anger camera.

Detector 2 may be capable of rotating around, or moving along, a desired trajectory relative to the body to acquire data at multiple predetermined positions from multiple views around the body.

Detector 2 may be provided with restricting means 10 establishing angles of incidence of gamma rays on the detector in a restricted range. It is noted that by angle of incidence it is meant the angle between the perpendicular to the surface of the detector and the ray path. Such means may be in the form of appropriate collimators. The collimator holes may be symmetric, such as circular or hexagonal shaped holes, or have different dimensions along the different axis, such as ellipse or rectangular shape holes. Furthermore, the shape of the bore of the collimators may be cylindrical, conic or other converging shapes.

In operation, detector 2 acquires radioisotope gamma ray photons 3, which are emitted from portion 4 of body 5 and passing through restricting means 10. The gamma photons impinge the photon detector crystal 6. If the crystal 6 is a semiconductor crystal, then the crystal converts the photons into electric signals, which are fed into a position logic circuitry 7 for processing. Alternatively, if the crystal is a scintillation crystal such as NaI, that utilize photo-multipliers, then the crystal converts photons 3 into scintillation light, which is thereafter, transformed into electric signals by photo-multiplier 9.

As a result of the processing, the electric signals are transformed into data indicative of photon energy and positions on the photon detector crystal 6 in which the photons impinge the detector.

The data that includes the position at which each photon impinged the detector, for each position of the detector, is termed projection. Thereafter, the projections are fed into a data analysis computer 8 for the purpose of reconstructing an image of a spatial distribution of the pharmaceutical substance within the portion of the body by processing said data. The photon energy information is registered for the assessment of the amount of Compton scattering that is introduced in the acquisition. In general, there is one energy window around each peak of the radiopharmaceutical substance. The width of each window is preferably set as narrow as may be reasonable to the specific detector that is used, in order to reject as many scattered photons as possible.

Figure 1B:
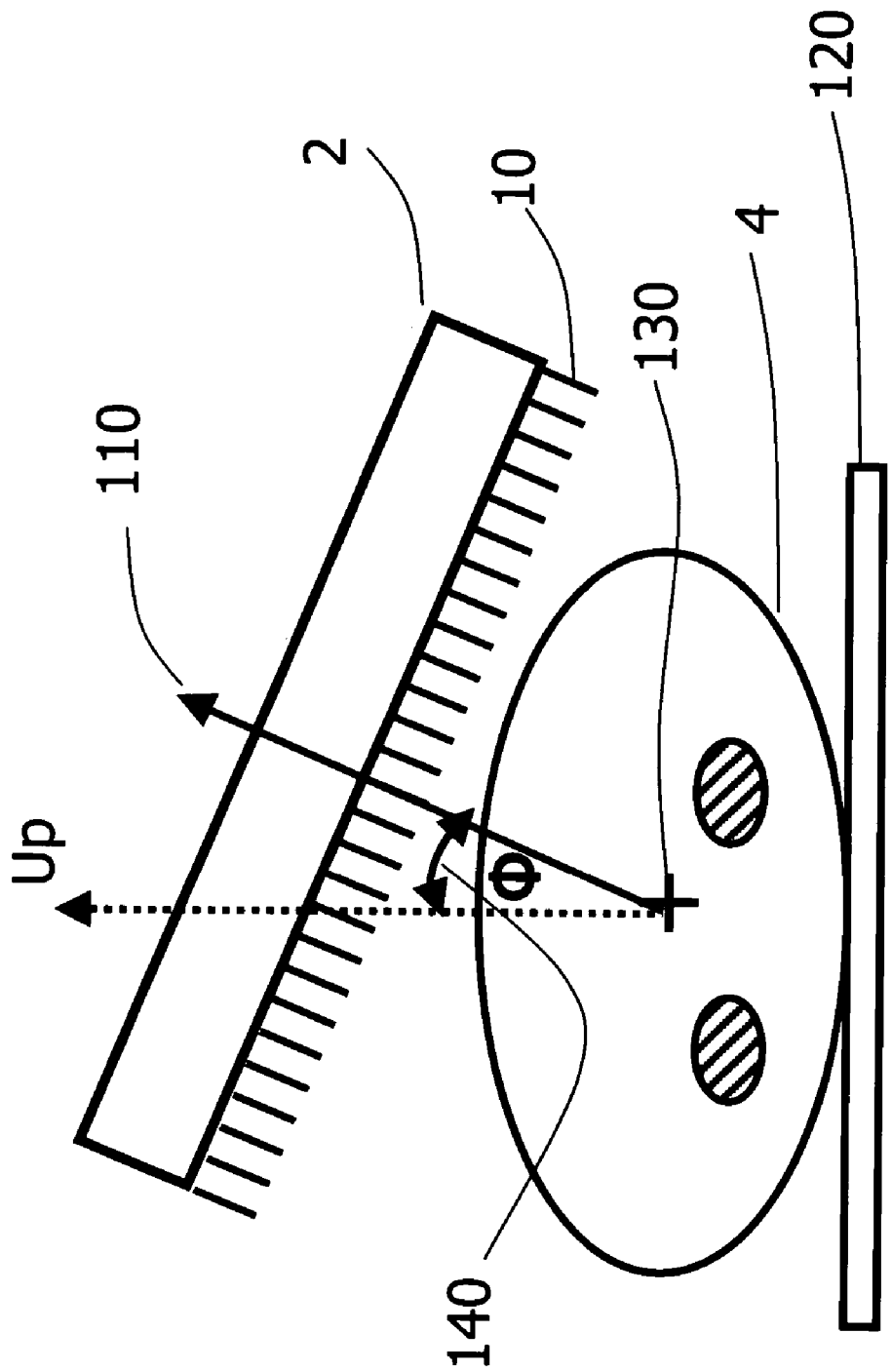
FIG. 1b illustrates angular projections.

FIG. 1b illustrate the convention used in arranging the data into angular projections. Detector 2 rotates around the portion of the patient 4 lying on patient table 120. In this illustration, the center of the coordinates system is chosen as the center of rotation 130 around which the detector 2 is rotated, and the angular starting direction is conveniently chosen as the vertical direction (up). The projection angle φ 140 is defined as the angle between the vertical direction (up) and the normal to the collimator face 110. It should be noted that this exemplary convention is arbitrary and other conventions may be used.

For example, in some gamma cameras, the detector is stationary and the patient is rotating about a vertical axis while seating in a rotating chair. Similar to the illustration of FIG. 1b, an arbitrary direction fixed to the patient is chosen, and the projection angle is measured between the arbitrary direction and the normal to the collimator face.

In some cameras, in order to decrease the data acquisition time, several detectors are used. In this case, several projections are measured at once, each assigned with an angular value measured between the arbitrary direction and the normal to the face of the collimator of the specific detector.

Two types of configurations are common:
1. Parallel configuration (known as "H" mode) in which the two detectors are on opposite sides of the patient so that if the first detector is acquiring an angular projection φ, while the second detector acquires angular projection φ+180 deg.
2. Right angle configuration (known as "L" mode) in which the two detectors are right angle to each other so that if the first detector is acquiring angular projection φ, then the second detector acquires angular projection φ+90 deg.

Other configurations are less popular.

In a typical acquisition, the detector stays stationary while data is acquired for the angular projection at projection angle $\phi_i$ corresponding to the position of the detector relative to the patient, then the detector advances to the next angular position and stops for acquiring the next angular projection at projection angle $\phi_{i+1}$. For FBP algorithm to reconstruct the image, the input data set containing projections covering at least 180 degrees of rotation must be used. Else, severe artifacts appear in the reconstructed image. This implies that a rotation of the camera of at least 180 degrees is necessary for single-detector or dual-detector camera in H-mode, and at least 90 degrees rotation is necessary for dual-detector camera in L-mode.

Angular separation between projections d $\phi = \phi_{i+1} - \phi_i$ affects the spatial resolution of the FBP-reconstructed image. Typical values of 2 or 3 degrees between adjacent angular projections are used in order to reduce artifacts and maintain clinically acceptable image quality.

Since the detector assembly, which comprises of detector, radiation shields and a collimator is heavy, rotating the detectors requires strong electrical motors and generally the time it takes to rotate the camera between positions is several seconds. Typically, the data acquisition is stopped during the detector motion to prevent image blurring Thus, the larger the number of projections, the larger the portion of ill-spent dead time during actual data acquisition For example, if it takes 2 seconds to accelerate, rotate, decelerate and stop a single-detector, then during the acquisition procedure of 90 angular projections separated by 2 degrees, three minutes of dead time are wasted on detector motion. This may add about 16.7% to an acquisition for which 12 seconds are used for data acquisition at each angular position and increases the total imaging time from 18 to 21 minutes.

Shortening the total acquisition time is possible mainly by reducing the number of projections acquired, the acquisition duration at each position or both.

Figure 2A:
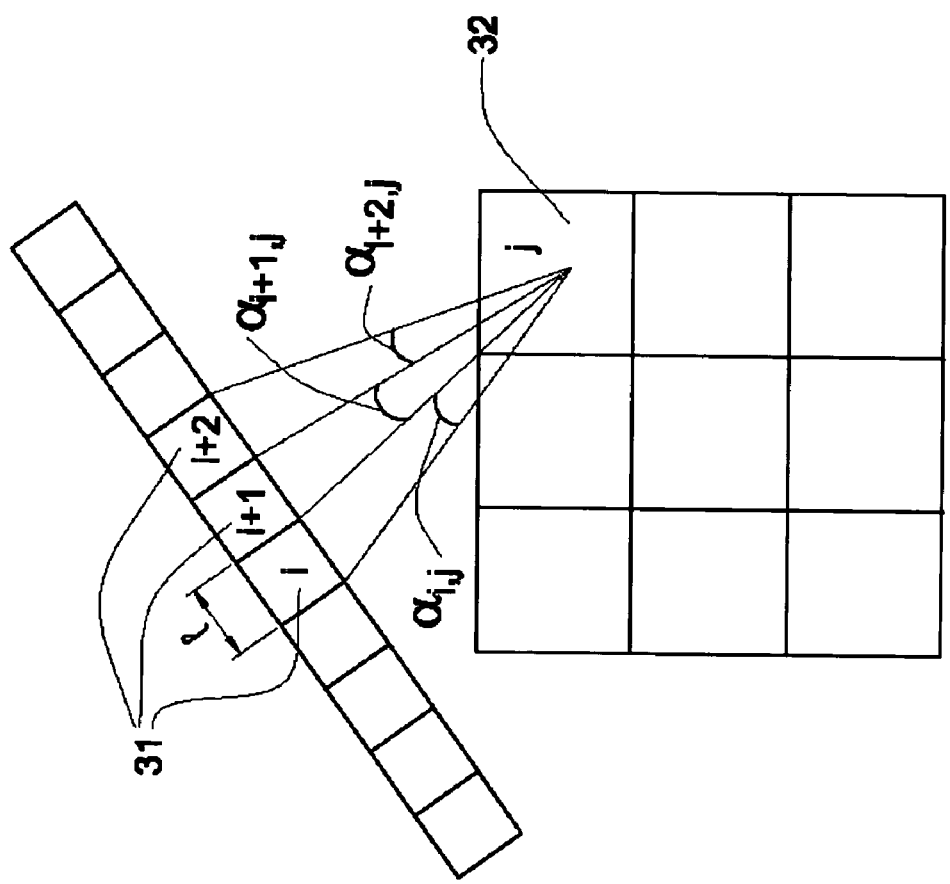
FIG. 2a is an exemplary flow chart of the acquisition procedure and the iterative reconstruction algorithm in accordance with the present invention.

FIG. 2a depicts the method of acquiring and reconstructing medical images according to a preferred embodiment of the current invention.

The patient is injected with a standard, clinically acceptable dosage of radiopharmaceutical and is placed on the examination table of the Gamma camera. The camera is set up to acquire data for duration lasting less than two thirds of the standard time used for the diagnostic procedure and optionally, preferably only one half to one third of that time. Optionally, this time reduction is achieved by reducing the number of angular projections acquired, keeping the time duration spent in acquiring each angular projection essentially the same as before. As a consequence, the angular separation between adjacent angular projections increases.

For example, a medical diagnostic procedure, commonly requiring acquisition of 60 projections separated by 3 degrees, would be performed according to the method of current invention, using no more than 45 angular projections separated by 4 degrees or less, for example 40, 30 or even only 20 angular projections.

Alternatively or additionally, the time duration spent in acquiring each angular projection may be shortened.

In some systems, it is possible to perform data acquisition in which some or all angular projections are visited more than once. For example, the camera may be set up to scan the portion of patient body several times during the data acquisition. Plurality of data acquired at the same angular position with respect to the patient is generally summed up or used as ordered sub-sets as will be described below.

Acquired information is stored and processed to form the reconstructed image on a remote processing station or on the computer used by the camera itself.

The iterative reconstruction algorithms, for example as shown in FIG. 2a, make better use of the available acquired data and enable to shorten the total acquisition time without substantially scarifying image quality and diagnostic utility.

The reconstruction of the image according to the present invention may be performed based on any appropriate iterative algorithm.

An example of such algorithm, based on weight values, which are functions of either angles or angles and distances between different elements of the portion of the body and corresponding elements of body's projection on the detector is detailed below (see WO 02/12918, incorporated herein by reference).

The reconstruction of the image may start from dividing an area of the detector facing the body onto M bins and dividing portion 4 of body 5 onto N voxels. As a result of such discretization, the photons are binned according to their position on the detectors and a set of values $D_{ik}$ (wherein i=1, ..., M) indicative of a number of photons acquired by the i-th bin, for any position k (wherein k=1, ..., L) at which the detectors are positioned while acquiring this data, is provided. Clearly, if the detector includes M crystals and each crystal is associated with a bin, then the step of additionally dividing of the detector's area onto M bins is unnecessary.

Further, a coupling between each bin of the detector at each position k at which the detectors are positioned while acquiring this data, and each voxel of the portion of the body is established. As a result of the coupling, a matrix $P=\{P_{ijk}\}$ of weight values of the voxels of the portion of the body (wherein i=1, ..., M, j=1, ..., N and k=1, ..., L) is constructed. For the rest of the discussion, the reference to the position k in the elements of the matrix P, and in the detector values D will be omitted.

Figure 2B:
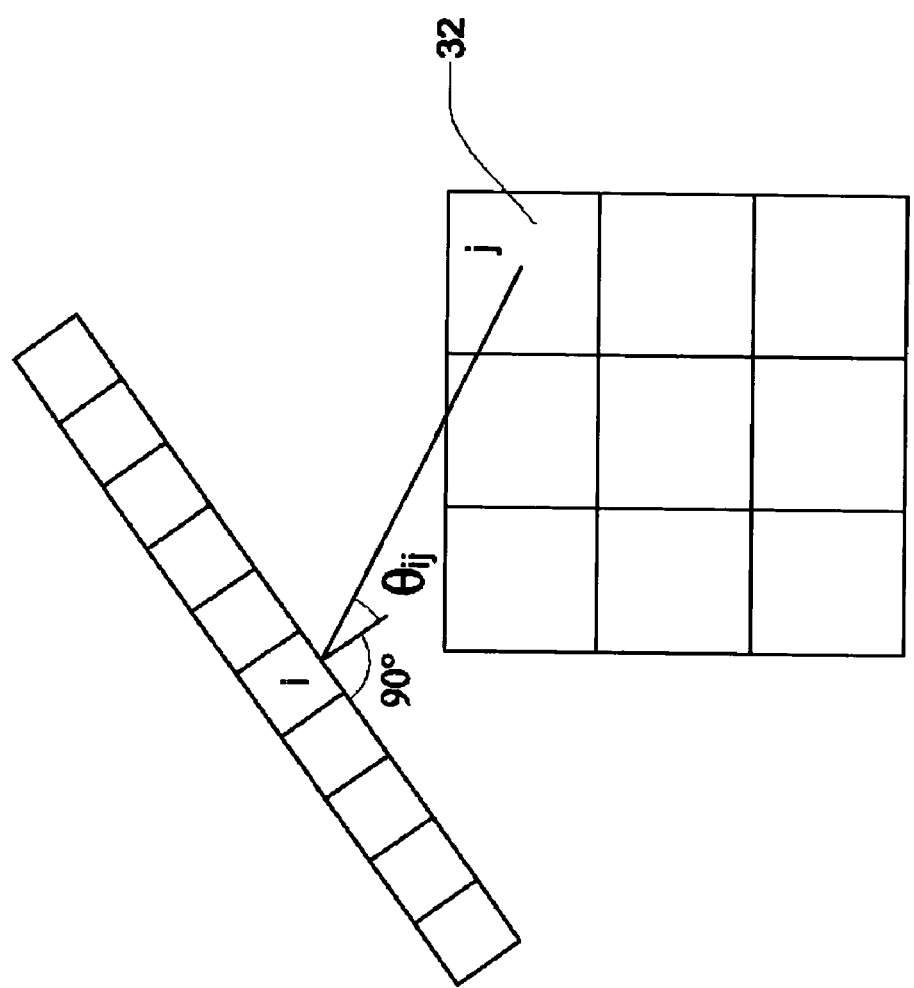
FIG. 2b is a simplified diagram depicting one example of coupling between different elements of the detector and corresponding elements of the body in accordance with the present invention.

FIG. 2b shows a simplified, two dimensional diagram depicting one example of the coupling between bins 31 having indices i, i+1, i+2, ... and a voxel 32 having an index j, which results in weight values $P_{ij}$, $P_{i+1,j}$, and $P_{i+2,j}$ that are functions of a set of angles $\alpha_{ij}$, $\alpha_{i+1,j}$, $\alpha_{i+2,j}$, ..., and possibly distances between the bins 31 and voxel 32. Since collimators are used, a photon that emanated from voxel i and is within the angle of view of a given bin, maybe absorbed by the walls of the collimator at that area. Therefore, the $P_{ij}$ should be multiplied by the relative effective area of bin i as viewed from voxel j. (see, for example, C. E. Metz, F. B. Atkins and R. N. Beck, "*The Geometric transfer function component for scintillation camera collimators with straight parallel holes*," Phys. Med. Biol., 1980, v. 25, p. 1059–1070).

According to a more general example, P may be a matrix in which each of the matrix elements $P_{ij}$ is a function of an average angle and possibly distance at which a detector bin having an index i is viewed from the voxel having an index j. Alternatively, the P may be a matrix in which each of the matrix elements $P_{ij}$ is a function of an angle and possibly distance at which the detector bin having an index i is viewed from a center of the voxel having an index j.

Figure 2C:
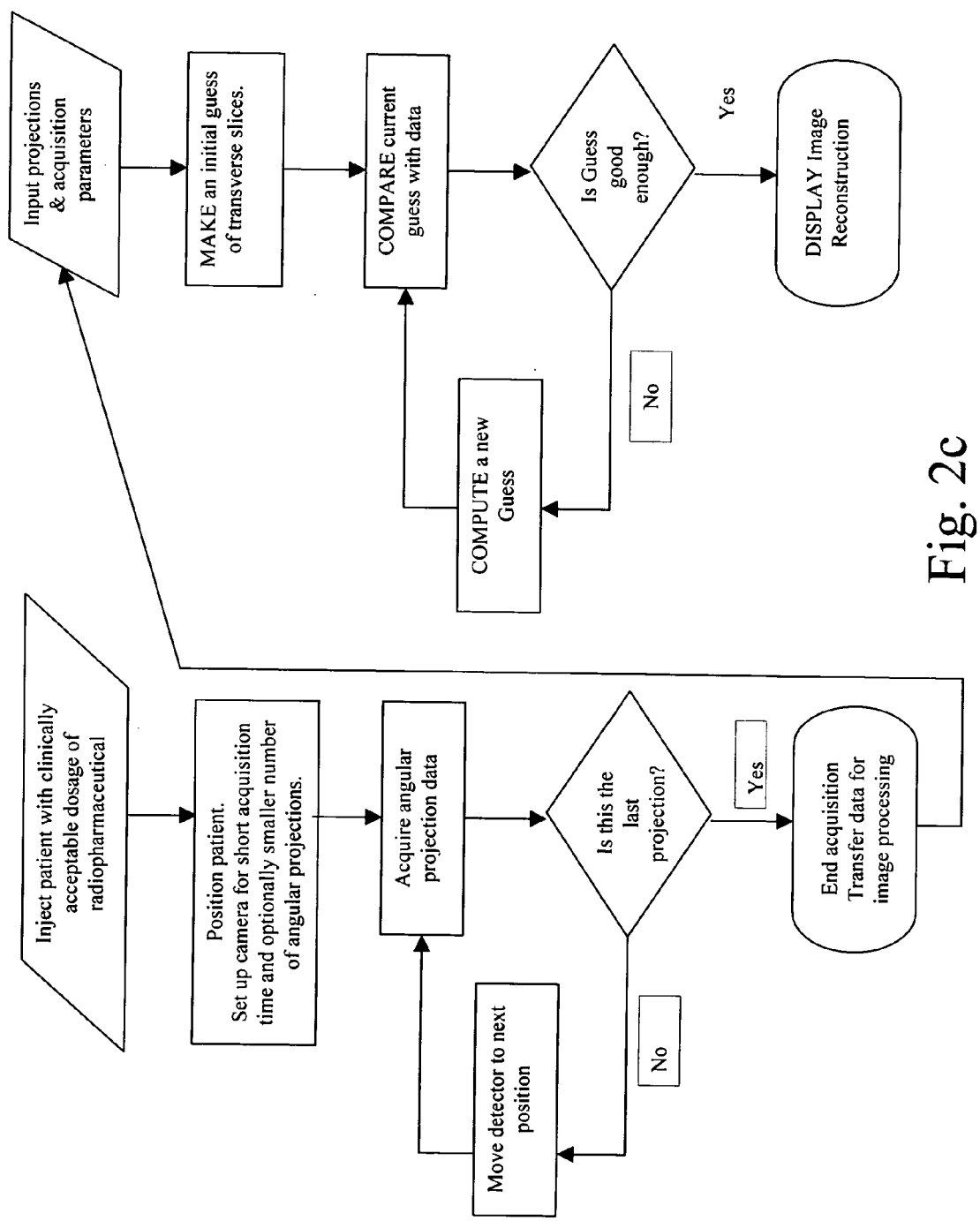
FIG. 2c is a simplified diagram depicting another example of coupling between different elements of the detector and corresponding elements of the body in accordance with the present invention.

FIG. 2c illustrates another example, in 2 dimensions, wherein P is a matrix in which its elements are presented by equation $$P_{ij} = c \frac{l \cos \Theta_i}{z^2},$$

wherein $\Theta_i$ is the angle at which the detector's bin having an index i views the voxel having an index j, c is a constant, l is the length of the detector bin's side, z is the distance between the centers of the voxel having index j and the bin having index i. As yet another example, the value of the angle $\Theta_i$ may be an average angle of view from the bin having an index i into the voxel having an index j.

In the most general case, the three dimensional case, the weights depend on the solid angle between a given point in a voxel and a given detector bin, on the position k of the detector relative to the starting point of the acquisition and on the distance of the voxel from the bin. As with the two-dimensional case, when collimators are used, these weights are multiplied by the relative effective area of the bin associated with that solid angle.

The elements of the matrix P may be modified to incorporate the attenuation effect, when attenuation map is available. The modification is such that the $P_{ij}$ as described above, will take into account the attenuation terms that are associated with the voxels through which the ray emanated at voxel j pass to arrive at bin i, when the detectors are in position k. (see, for example, D. L. Baiely, B. F. Hutton & P. J. Walker, "*Improved SPECT Using Simultaneous Emission and Transmission Tomography*", J Nucl Med, 1987, 28: 844–851).

In order to derive voxel values $V_j$ of an image of the portion of the body and thereby to obtain a spatial distribution of the pharmaceutical substance indicating the functional information on this portion of the body, a mathematical model should be formulated and solved. Formulation of the mathematical model includes modelling a relation between the set of values $D_i$ and a set of unknown voxel values $V_j$ of the image.

As one example, the mathematical problem for deriving $V_j$ may be formulated as a set of algebraic equations $$D_i = \sum_{j=1}^{N} P_{ij} V_j$$

with respect to each unknown value $V_j$ may be solved, wherein j=1, ..., N and i=1, ..., M As it can be clear to a man of the art, the set of equations in a general form is:

$$D_i = \sum_{j=1}^{N} P_{ij} V_j + E_i,$$

i.e. also includes a set of measurement errors $E_i$.

As another example, the mathematical problem maybe formulated as an optimization problem with a likelihood function that should be solved for deriving the unknown values $V_j$ (see, for example, the technique of L. A Shepp and Y. Vardi, "*Maximum likelihood reconstruction for emission tomography*," IEEE Trans Med. Imaging, 1982, v. 1, p. 113–122, or K. Lange and R. Carson, "*EM reconstruction algorithm for emission tomography*," J. Comput. Assist. Tomogr., 1984, v. 8, p. 306–316).

As yet another example, the mathematical problem may be formulated as least squares (possibly weighted least squares) with Gaussian or Poisson noise, and then solved for the unknowns, Vj, by means of singular value decomposition, or any other optimization algorithm such as the steepest decent algorithm. (references for these methods, see for example William H. Press et al, "*Numerical Recipes in C++*", Cambridge University Press, Chapter 2,)

The optimization problem may be formulated as a statistical model of the emission process for estimating image data. According to the model, the number of photons $V_j$ that are emitted from a voxel with an index j obeys the Poisson distribution $$P(V_j = n) = \frac{e^{-\lambda(V_j)} \lambda(V_j)^n}{n!},$$

wherein $P(V_j=n)$ is the probability of having n events of photon emissions in the j-th voxel, and $\lambda(V_j)$ is the unknown mean value of the Poisson distribution. Further, the number of photons $D_i$ that are acquired by the i-th bin also obeys the Poisson distribution with mean value of the distribution $\lambda(D_i)$. The random variables $V_j$ and $D_i$ as well as their respective mean values $\lambda(V_j)$ and $\lambda(D_i)$ are, correspondingly, related via the following equations $$D_i = \sum_{j=1}^{N} P_{ij} V_j \text{ and } \lambda(D_i) = \sum_{j=1}^{N} P_{ij} \lambda(V_j).$$

Thus the optimization problem is used to estimate the mean value $\lambda(V_j)$ of the Poisson random variables $V_j$, using the $D_i$ values measured by the detector. For example, one conventional statistical approach for determination of $V_j$ is to find a maximum of the likelihood function $$L[\lambda(D_i)] = \prod_{i=1}^{M} \frac{e^{-\lambda(D_i)} \lambda(D_i)^{D_i}}{D_i!},$$

with respect to the unknowns $V_j$.

An image of the portion of the body reconstructed by utilizing the algorithms described above may be a two dimensional image or a three dimensional image of the portion of the body.

As yet another example, the mathematical problem may be formulated as a Bayesian optimization problem, in which a likelihood function is utilized together with a penalty function known per se. (See for example, P. J. Green, *Bayesian reconstruction from emission tomography data using a modified FM algorithm*, IEEE Trans Med. Imaging, 1990, v. 9, p. 84–93, or P. J. Green, *On the use of the EM algorithm for penalised likelihood estimator*, J. Roy. Statist. Soc. (B), 1990, 52:443–452, or D. Geman and G. Reynolds, *Constraint Restoration and the Recovery of Discontinuities*, IEEE trans on Pattern Analysis and Machine Intelligence, 1992, v. 14, p. 367–383.) This optimization problem should be solved for deriving the unknown values $V_j$. As an example, but not limited to, a general form of the Bayesian optimization problem can be written as follows:

$$V = \arg\max\{L[\lambda(D_i)] + \alpha F(V_j, V_k)\},$$

where $\alpha$ is the weight that is given to the prior function F.

For instance the penalty function may be chosen in the form of $$F(V_j, V_k) = \sum_{j,k} (V_j - V_k)^2,$$

wherein the sum is taken over two neighbouring voxels having indices j and k. Such a penalty function expresses some prior knowledge about the smoothness characteristics of the reconstructed image. Other penalty functions, which preserve discontinuities are more adequate for SPECT reconstruction.

Ordered Subset Expectation Maximization (OSEM) is a modification of an iterative algorithm in which at least in few of the iterations, only sub set of the entire available data is used. OSEM algorithms reduce the amount of computation needed for each iteration and thus reduce the overall computation time.

As it can be clear to a person skilled in the art, the choice of the optimally minimal number of angular projections and the duration of data acquisition in each position utilized for a scan, is guided by the trade-offs between scan duration and image quality that can be accepted. Factors, for instance, such as collimator type, isotope used and dosage injected, patient body size; diagnostic procedure and the location of the studied organs should also be taken into account. Hence, practical solutions will depend on the factors mentioned above and can be optimized accordingly.

For example, in cardiac imaging, collimator characteristics are guided by the priority to have a high sensitivity image rather than high resolution one, whereas for brain perfusion images, because of the brain's fine structures, high resolution is required.

Another parameter that strongly affects both data acquisition time and image quality is the number of pixels in the image. In some cases, for example when examination time needs to be shortened due to the patient inability to stay immobile for long duration, smaller matrix size is chosen to allow shorted data acquisition. For example, bone scan procedure which usually is performed using 128 by 128 projection matrix size and 128 by 128 voxels for each reconstructed slice of the three dimensional image and requires 18 to 30 minutes of data acquisition time, may be performed in 12 minutes if matrix size of only 64 by 64 pixels is selected. The reduction in matrix size reduces the resolution of the reconstructed image.

Using an iterative algorithm according to the current invention, allows successfully performing bone scan procedure using 128 by 128 matrix size with data acquired in 9 to 10 minutes without scarifying resolution or image quality.

An iterative algorithm according to the current invention may be applied to data acquired both in the form of angular projections and in List-Mode. In some systems, List-Mode data acquisition may be performed while the detector rotates continuously around the patient. In these systems, the data set includes information that enables determination of the angular projection φ for each recorded photon. The data may later undergo discretization and be binned to projections before reconstruction. Alternatively, the data set as is may be used in the iterative algorithm.

Figure 3C:
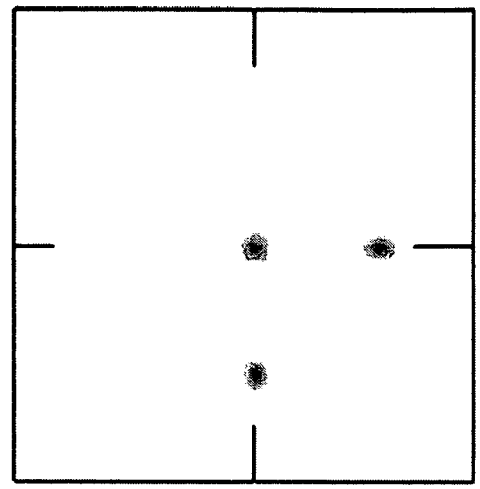
FIG. 3c is a reconstructed image of the same phantom of FIG. 3a taken with the reduced set of 40 angular projections as in FIG. 3b and reconstructed using iterative algorithm according to a preferred embodiment of the present invention and not showing the star-like artifact and of superior image quality.
Figure 3B:
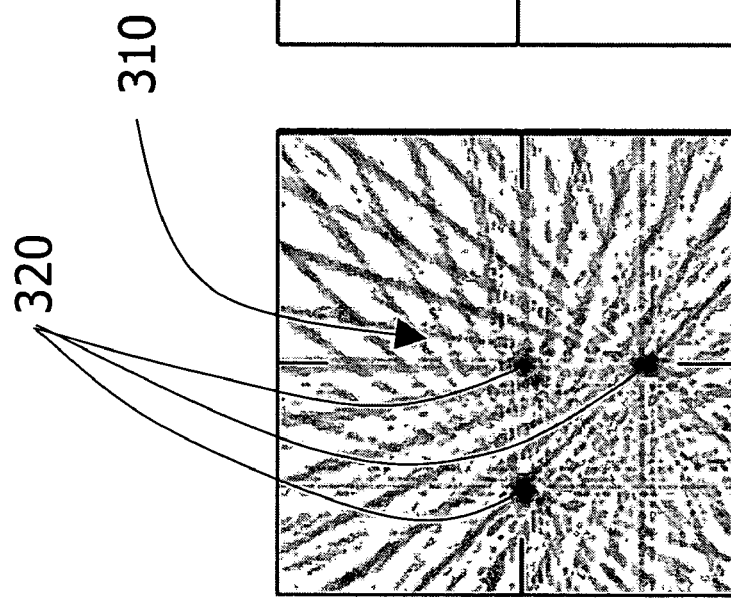
FIG. 3b is a reconstructed image of the same phantom of FIG. 3a taken using a reduced set of only 40 angular projections and reconstructed using FBP algorithm; showing a characteristic star-like artifact.
Figure 3A:
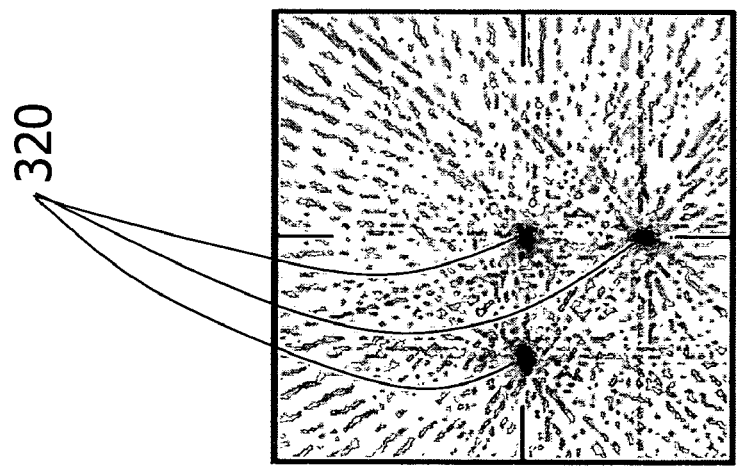
FIG. 3a is a reconstructed image of a phantom taken with full set of 120 angular projections and reconstructed using Filtered Back Projection (FBP) algorithm (known in the art).

FIGS. 3a, 3b and 3c illustrate the artifact associated with reduction of the number of angular projections:

FIG. 3a is a reconstructed image of a phantom taken with full set of 120 angular projections acquired at angular separation between projections of 3 degrees and reconstructed using Filtered Back Projection (FBP) algorithm as known in the art resulted in satisfactory image quality. Some artifacts associated with the reconstruction are faintly seen.

FIG. 3b shows a reconstructed image of the same phantom of FIG. 3a taken with reduced set of only 40 angular projections acquired at angular separation between projections of 9 degrees, having the same acquisition time per projection. Total data acquisition was thus one third of the time used to acquire the data used for FIG. 3a. Reconstruction using FBP algorithm as known in the art resulted in a visible characteristic star-like artifact 310 centered on each location of high concentration of radiopharmaceutical 320. The star-like artifact, not only degrades the visual appearance of the reconstructed image, but it also adversely affects the effective resolution of the image as it broadens any reconstructed feature. Artifacts may falsely appear as image features.

FIG. 3c is a reconstructed image of the same phantom using the same reduced set of only 40 angular projections as in FIG. 3b and reconstructed using an iterative algorithm according to the current invention and not showing the star-like artifact. Although the data set used for reconstruction of FIG. 3c is only one third of the data set used for reconstruction of FIG. 3a, image quality is superior and resolution is better. In fact, further reduction of the data set (and thus, reduction of the acquisition time) is possible before the quality of reconstructed image according to the current invention will match or degrade below the image quality of FIG. 3a.

It should be noted that the inventive use of the iterative reconstruction according to the current invention has at least the following advantages: It allows the reduction of number of angular projection used for the reconstruction without creating artifacts and while preserving spatial resolution, it preserves the image quality as judged by image smoothness and visual clarity in spite of substantial reduction of the number of detected photons used to create the data set.

During typical clinical imaging, as illustrated in FIGS. 4a, 4b and 4c, angular separation between projections d ϕ may be increased from 3 degrees as used in the art to 6 or even 9 degrees without changing any of the other data acquisition parameters such as acquisition time per projection, leading to a twofold or even threefold decrease in total imaging time. Yet using iterative algorithm such as the weight based iterative reconstruction method results in similar or even superior reconstructed image quality.

FIG. 4a is a reconstruction image of a pelvis of a child who was injected with a dosage of 30 mCi of Tc-99m isotope. Data was acquired using a dual-detector camera-"Varicam" made by General Electric. The camera was equipped with a standard low-energy general-purpose VPC40 collimator having 86300 holes with 1.5 mm hole diameter, 0.2 mm wall thickness and 31 mm hole length. The camera, having two detectors, acquires two angular projections at the same time, Total of 120 angular projections, separated by 3 degrees and spanning full 360 degrees were taken at 20 seconds acquisition duration per projection. Total acquisition time was 20 minutes giving effective acquisition time of 40 minutes.

FIG. 4b is a reconstructed image of the same pelvis taken at identical conditions as in FIG. 4a, except that the total number of angular projections was only 40, separated by 9 degrees. Total acquisition time was only 6 minutes and 40 seconds, giving effective acquisition time of 13 minutes and 20 seconds. The reconstruction algorithm used in the art is incapable of reconstructing a clinically useful image Artifacts 412 are clearly seen.

FIG. 4c is a reconstruction image of the same pelvis taken at identical conditions as in FIG. 4b (total of 40 angular projections). Using iterative reconstruction algorithm according to the current invention resulted in clinically acceptable image, very similar to the image seen in FIG. 4a. Careful comparison of the resolution as judged by the clarity of the pelvis bone 410 and 414 in FIGS. 4a and 4c respectively, shows the slightly better quality of the image acquired and reconstructed according to the current invention.

Table 1 below gives typical acquisition parameters clinically used for performing common medical diagnostic procedures. The table illustrates the advantages of using the method according to the current invention. The parameters given in the table are typical and may vary.

In this table, each listed medical procedure is identified by the following typical parameters: Isotope used, total span of angular projections and matrix size. For each procedure, for single-detector and dual-detector camera, the range of acquisition duration used in the art is given as well as the range of acquisition duration which is needed in order to obtain simile or superior image quality in accordance with the current invention.

TABLE 1

| SPECT application Isotope Total span of angular projections | Actual data acquisition duration (Effective acquisition time) In minutes Typical number of projections | | | |
|---|---|---|---|---|
| | Single-detector camera | | Dual-detector camera | |
| Number of pixels used | Art | Invention | Art | Invention |
| Bone SPECT Technetium 360 deg acquisition 128 × 128 or 64 × 64 matrix | 30–40 (30–40) 120, 128 | 10–20 (10–20) 40, 60, 64, 120, 128 | 15–20 (30–40) 120, 128 | 5–10 (10–20) 40, 60, 64, 120, 128 |
| Bone SPECT Technetium 180 deg acquisition 128 × 128 or 64 × 64 matrix | 17–20 (17–20) 60, 64 | 7–10 (7–10) 20, 30, 32, 60, 64 | 12–20 (24–40) 60–64 | 5–10 (10–18) 20, 30, 32, 60, 64 |
| Cardiac Technetium, Thallium 180 deg acquisition 64 × 64 matrix | 20–25 (20–25) 60, 64 | 10–12 (10–12) 20, 30, 32, 60, 64 | 12–18 (24–36) 60, 64 | 6–12 (12–20) 20, 30, 32, 60, 64 |
| Brain Technetium, Thallium 360 deg acquisition 128 × 128 matrix | 20–40 (20–40) 120, 128 | 10–20 (10–20) 40, 60, 64, 120, 128 | 20–30 (40–60) 120, 128 | 7–15 (14–30) 40, 60, 64, 120, 128 |
| Medium energy Oncology Gallium, Indium, Iodine 360 deg acquisition 128 × 128 or 64 × 64 matrix | 30–50 (30–50) 60, 64 120, 128 | 10–25 (10–25) 60, 64 120, 128 | 20–40 (40–80) 60, 64 120, 128 | 9–20 (18–40) 60, 64, 120, 128 |

In gated SPECT, image acquisition and image reconstruction maybe performed separately for each group of sub-projections using iterative algorithm according to the current invention. Consequently, data acquisition time may be reduced or the number of angular projection may be reduced or both.

It should be noted that the acquisition time spent at each detector's angular position should be long enough to include at least one full heartbeat cycle and preferably few heartbeat cycles in order to correctly reflect all phases of the heart contraction motion. Since patients scanned are naturally those with suspected heart problems, heartbeats may be irregular and data acquired during un-synchronizeable heartbeats may have to be rejected. In these cases, reducing the number of angular projections may be advantageous over reducing the time duration spent at each angular position.

In addition, it is possible to reconstruct an image of the totality of all the acquired data using iterative method or methods known in the art.

Attenuation map needed for performing attenuation correction of emission image may be reconstructed from angular attenuation projections, calculated from comparing the number of photons transmitted through the patient to the number of photons detected in the absence of the patient.

Attenuation map may be acquired and reconstructed using iterative method according to the current invention. Consequently, data acquisition time may be reduced or the number of angular projection may be reduced or both.

When emission data is gated, attenuation data may have to be gated as well to reflect the motion of the patient chest during heartbeats. In these cases, reducing the number of angular projections may be advantageous over reducing the time duration spent at each angular position.

While the invention has been described with reference to certain exemplary embodiments, various modifications will be readily apparent to and may be readily accomplished by persons skilled in the art without departing from the spirit and scope of the above teachings.

It should be understood that features and/or steps described with respect to one embodiment may be used with other embodiments and that not all embodiments of the invention have all of the features and/or steps shown in a particular figure or described with respect to one of the embodiments. Variations of embodiments described will occur to persons of the art.

It is noted that some of the above described embodiments may describe the best mode contemplated by the inventors and therefore include structure, acts or details of structures and acts that may not be essential to the invention and which are described as examples. Structure and acts described herein are replaceable by equivalents which perform the same function, even if the structure or acts are different, as known in the art. Therefore, the scope of the invention is limited only by the elements and limitations as used in the claims. The terms "comprise", "include" and their conjugates as used herein mean "include but are not necessarily limited to"

The invention claimed is:

1. A method of diagnostic imaging in shortened acquisition time for obtaining a reconstructed diagnostic image of a portion of a body of a human patient who was administered with dosage of radiopharmaceutical substance radiating gamma rays, using SPECT (single photon emission computerized tomography), for determination of functional information thereon, comprising the steps of:
   (a) acquiring photons emitted from said portion of the body, by means of at least one detector capable of converting the photons into electric signals, said detector comprises a collimator having a plurality of elongated bores, wherein acquiring photons emitted from said portion of the body comprises acquiring adjacent angular projections separated by at least 5 degrees;
   (b) processing said electric signals by a position logic circuitry and thereby deriving data indicative of positions on said at least one detector, where the photons have impinged the detector; and
   reconstructing a diagnostic image of a spatial distribution of the pharmaceutical substance within the portion of the body by iteratively processing said data, said iteratively processing comprises utilizing weight values derived from functions of either solid angles or solid angles and distances between different discrete elements of the portion of the body and corresponding discrete elements of the angular projection of the portion of the body on the detector.

2. The method of claim 1 wherein acquiring photons emitted from said portion of the body comprises acquiring adjacent angular projections separated by at least 6 degrees.

3. The method of claim 1 wherein acquiring photons emitted from said portion of the body comprises acquiring adjacent angular projections separated by at least 7 degrees.

4. The method of claim 1 wherein acquiring photons emitted from said portion of the body comprises acquiring adjacent angular projections separated by at least 8 degrees.

5. The method of claim 1 wherein acquiring photons emitted from said portion of the body comprises acquiring adjacent angular projections separated by at least 9 degrees.

6. A method of diagnostic imaging in shortened acquisition time for obtaining a reconstructed diagnostic image of a portion of a body of a human patient who was administered with dosage of radiopharmaceutical substance radiating gamma rays, using SPECT (single photon emission computerized tomography), for determination of functional information thereon, comprising the steps of:
   c) acquiring photons emitted from said portion of the body, by means of at least one detector capable of converting the photons into electric signals, said detector comprises collimator having a plurality of elongated bores, wherein the effective acquisition time for obtaining the data required for forming said reconstructed diagnostic image is less than 16 minutes;
   d) processing said electric signals by a position logic circuitry and thereby deriving data indicative of positions on said at least one detector, where the photons have impinged the detector; and
   e) reconstructing a diagnostic image of a spatial distribution of the pharmaceutical substance within the portion of the body by iteratively processing said data, said iteratively processing comprises utilizing weight values derived from functions of either solid angles or solid angles and distances between different discrete elements of the portion of the body and corresponding discrete elements of the angular projection of the portion of the body on the detector.

7. The method of claim 6 wherein the effective acquisition time is less than 14 minutes.

8. The method of claim 6 wherein the effective acquisition time is less than 12 minutes.

9. The method of claim 6 wherein the effective acquisition time is less than 10 minutes.

10. The method of claim 6 wherein the effective acquisition time is less than 8 minutes.

11. The method of claim 6, wherein the photons are acquired in a list-mode procedure.

12. A method of diagnostic imaging in shortened acquisition time for obtaining a reconstructed diagnostic image of a portion of a body of a human patient who was administered with dosage of radiopharmaceutical substance radiating gamma rays, using SPECT (single photon emission computerized tomography), for determination of functional information thereon, comprising the steps of:
   (a) acquiring photons emitted from said portion of the body, by means of at least one detector capable of converting the photons into electric signals, said detector comprises at least one detector crystal and a collimator having a plurality of elongated bores, wherein acquiring photons emitted from said portion of the body comprises acquiring angular projections, and wherein the total time of photon acquisition for obtaining the data required for forming said reconstructed diagnostic image is less than 20 minutes;
   (b) processing said electric signals by a position logic circuitry and thereby deriving data indicative of positions on said at least one detector, where the photons have impinged the detector; and
   (c) reconstructing an diagnostic image of a spatial distribution of the pharmaceutical substance within the portion of the body by iteratively processing said data, said iteratively processing comprises utilizing weight values derived from functions of either solid angles or solid angles and distances between different discrete elements of the portion of the body and corresponding discrete elements of the angular projection of the portion of the body on the detector.

13. The method of claim 12 wherein:
said radiopharmaceutical comprises Technetium;
said at least one detector comprises a single detector;
the angular projections span about 360 degrees; and
said diagnostic imaging comprises bone SPECT.

14. The method of claim 12 wherein:
said radiopharmaceutical comprises Technetium;
said at least one detector comprises two detectors;

the angular projections span about 360 degrees;
the total time of photon acquisition is less than 10 minutes; and
said diagnostic imaging comprises bone SPECT.

15. The method of claim 12 wherein:
said radiopharmaceutical comprises Technetium;
said at least one detector comprises a single detector;
the angular projections span about 180 degrees;
the total time of photon acquisition is less than 13 minutes; and
said diagnostic imaging comprises bone SPECT.

16. The method of claim 12 wherein:
said radiopharmaceutical comprises Technetium;
said at least one detector comprises two detectors;
the angular projections span about 180 degrees;
the total time of photon acquisition is less than 10 minutes; and
said diagnostic imaging comprises bone SPECT.

17. The method of claim 12 wherein:
said radiopharmaceutical comprises an isotope selected from the group of Technetium and Thallium;
said at least one detector comprises a single detector;
the angular projections span about 180 degrees;
the total time of photon acquisition is less than 15 minutes; and
said diagnostic imaging comprises cardiac imaging.

18. The method of claim 12 wherein:
said radiopharmaceutical comprises an isotope selected from the group of Technetium and Thallium;
said at least one detector comprises two detectors;
the angular projections span about 180 degrees;
the total time of photon acquisition is less than 10 minutes; and
said diagnostic imaging comprises cardiac imaging.

19. The method of claim 12 wherein:
said radiopharmaceutical comprises an isotope selected from the group of Technetium and Thallium;
said at least one detector comprises a single detector;
the total time of photon acquisition is less than 15 minutes; and
said diagnostic imaging comprises brain SPECT.

20. The method of claim 12 wherein:
said radiopharmaceutical comprises an isotope selected from the group of Technetium and Thallium;
said at least one detector comprises two detectors;
the total time of photon acquisition is less than 15 minutes; and
said diagnostic imaging comprises brain SPECT.

21. The method of claim 12 wherein:
said radiopharmaceutical comprises an isotope selected from the group of Gallium, Indium and Iodine;
said at least one detector comprises a single detector;
the total time of photon acquisition is less than 25 minutes; and
said diagnostic imaging comprises Medium energy Oncology SPECT.

22. The method of claim 12 wherein:
said radiopharmaceutical comprises an isotope selected from the group of Gallium, Iodine and Indium;
said at least one detector comprises two detectors;
the total time of photon acquisition is less than 20 minutes; and
said diagnostic imaging comprises Medium energy Oncology SPECT.

23. The method of claim 12, wherein the photons are acquired in a list-mode procedure.

24. A method of shortening acquisition time for obtaining a reconstructed diagnostic image of a portion of a body of a human patient who was administered with dosage of radiopharmaceutical substance radiating gamma rays, using SPECT (single photon emission computerized tomography), for determination of functional information thereon, comprising the steps of:

(a) acquiring photons emitted from said portion of the body, by means of a detector capable of converting the photons into electric signals, said detector comprises a collimator having a plurality of elongated bores, wherein the total time of photon acquiring for obtaining the data required for forming said reconstructed diagnostic image is equal to, or less than, three quarters of the clinically acceptable acquisition time;

(b) processing said electric signals by a position logic circuitry and thereby deriving therefrom data indicative of positions on said photon detector crystal, where the photons have impinged the detector; and (c) reconstructing an image of a spatial distribution of the pharmaceutical substance within the portion of the body by iteratively processing said data, said iteratively processing comprises utilizing weight values derived from functions of either solid angles or solid angles and distances between different discrete elements of the portion of the body and corresponding discrete elements of the angular projection of the portion of the body on the detector.

25. The method of claim 23 wherein said total time of photon acquiring is equal or less than two thirds of the clinically acceptable acquisition time.

26. The method of claim 23 wherein said total time of photon acquiring is less than one half of the clinically acceptable acquisition time.

27. The method of claim 23 wherein said total time of photon acquiring is equal or less than one third of the clinically acceptable acquisition time.

28. The method of claim 23 wherein said iteratively processing said data comprises arranging the data in angular projections.

* * * * *